(12) United States Patent
Sun et al.

(10) Patent No.: US 8,815,913 B2
(45) Date of Patent: Aug. 26, 2014

(54) METAL-CATALYZED COPOLYMERIZATION OF IMINES AND CARBON MONOXIDE AS A ROUTE TO SYNTHESIZE POLYPEPTIDES

(75) Inventors: Huailin Sun, Tianjin (CN); Jian Zhang, Tianjin (CN); Qiuhua Liu, Tianjin (CN); Lei Yu, Tianjin (CN); Jiangyu Zhao, Tianjin (CN)

(73) Assignee: Nankai University, Tianjin (CN)

( * ) Notice: Subject to any disclaimer, the term of this patent is extended or adjusted under 35 U.S.C. 154(b) by 612 days.

(21) Appl. No.: 12/480,675

(22) Filed: Jun. 8, 2009

(65) Prior Publication Data

US 2009/0264619 A1 Oct. 22, 2009

Related U.S. Application Data

(63) Continuation of application No. PCT/CN2007/003465, filed on Dec. 6, 2007.

(30) Foreign Application Priority Data

Dec. 6, 2006 (CN) .......................... 2006 1 0129890
Dec. 5, 2007 (CN) .......................... 2007 1 0195204

(51) Int. Cl.
*A61K 38/00* (2006.01)
*C07K 5/00* (2006.01)
*C07K 7/00* (2006.01)
*C07K 16/00* (2006.01)
*C07K 17/00* (2006.01)
*C07K 2/00* (2006.01)
*C07K 4/00* (2006.01)
*C07K 14/00* (2006.01)
*C07K 1/08* (2006.01)
*C07K 1/02* (2006.01)

(52) U.S. Cl.
CPC .. *C07K 1/088* (2013.01); *C07K 1/02* (2013.01)
USPC .......................................... 514/333; 530/300

(58) Field of Classification Search
CPC ........... A63H 27/08; C07K 1/02; C07K 1/088
See application file for complete search history.

(56) References Cited

U.S. PATENT DOCUMENTS 5,480,971 A * 1/1996 Houghten et al. ............ 530/328

OTHER PUBLICATIONS

Zask et al. ("Synthesis and Biological Activity of Analogues of the Antimicrotubule Agent N,b,b-Trimethyl-L-phenylalanyl-N1-[(1S,2E)-3-carboxy-1-isopropylbut-2-enyl]-N1,3-dimethyl-L-valinamide (HTI-286)," J. Med. Chem. 2004, 47, 4774-4786).*
Kalinovskaya et al. ("Characterization of Surfactin-like Cyclic Depsipeptides Synthesized by *Bacillus pumilus* from Ascidian Halocynthia aurantium," Mar. Biotechnol. 2002, 4, 179-188).*
Guryanov et al. ("Turn and Helical Peptide Spacers: Combined Distance and Angular Dependencies in the Exciton-Coupled Circular Dichroism of Intramolecularly Interacting bis-Porphyrins," Biopolymers, Mar. 2006, 82, 482-490).*
Cosani et al. ("N-Substituted Poly(a-amino acids). 2. Conformational Properties of Poly(y-ethyl N-methyl-L-glutamate) in Various Solvent Mixtures", Macromolecules, 1979, 12, 875-877).*
Meunier, Molecular Weight Determinations, Handbook of Instrumental Techniques for Analytical Chemistry, edited by Settle, 1997, pp. 853-.866.*
Cosani et al. Communications to the Editor. N-Substitutes Poly-alpha-Amino Acids. III. Synthesis and Conformation Properties of Poly(N-Methyl-L-Glutamic Acid), Bioplymers, vol. 21, 1982, pp. 471-474.*
Cosani et al. Pli(alpha-Aminoacidi)-N-sostituiti: Propieta' conformazionali. Cony. Ital. Sci. Macromol. Univ. Genova. 1$^{st}$ Chim Ind., 1979, Genoa, Italy, pp. 266-268.*
Conti. The helix-coil transition in polypeptides studied by NMR. Rendiconti del Seminario della Facolat di Scienze dell' Universita di Cagliari. 1968, vol. 38, pp. 391-404.*
Zhang et al. Poly-N-methylated alpha-peptides: synthesis and X-ray structure determination of beta-strand forming foldamers. Chem. Commun. 2006, pp. 497-499.*
Goodman et al. Conformational stuides of polypeptides and polydepsipeptides. Pept., Polypeptides Proteins, Proc. Rehovot Symp, 2$^{nd}$ part. 1974, pp. 126-145.*

* cited by examiner

*Primary Examiner* — Marcela M Cordero Garcia
(74) *Attorney, Agent, or Firm* — George G. Wang; Bei & Ocean

(57) ABSTRACT

Polypeptides of formula (I):

$$\left[\begin{array}{c} \text{N} - \overset{\text{H}}{\underset{\text{R}^2}{\text{C}}} - \overset{\overset{\text{O}}{\|}}{\text{C}} \\ \text{R}^1 \end{array}\right]_n \quad \text{(I)}$$

wherein $R^1$ and $R^2$ are substituents independently selected from substituted and un-substituted alkyl groups and substituted and un-substituted aryl groups, and n is an integer greater than or equal to 2. Synthesis methods are also provided that do not use amino acids as starting materials, but instead employ imines and carbon monoxide as monomers that undergo transition metal-catalyzed alternating copolymerization to directly provide polypeptides using an acylcobalt catalyst with the following structural formula:

$$R \underset{}{\overset{\overset{\text{O}}{\|}}{\diagdown}} Co(CO)_4$$

wherein R is selected from the group consisting of alkyl, phenyl, and substituted phenyl groups.

19 Claims, No Drawing

METAL-CATALYZED COPOLYMERIZATION OF IMINES AND CARBON MONOXIDE AS A ROUTE TO SYNTHESIZE POLYPEPTIDES

CROSS REFERENCE TO RELATED APPLICATIONS

This application claims priority benefit under 35 U.S.C. §120 of PCT/CN07/03465, which, in turn, claims priority benefit under the Paris Convention of Chinese Patent Application No. 200610129890.1, filed Jun. 12, 2007, and Chinese Patent Application No. 200710195204.5, filed May 12, 2007. The contents of all three applications are hereby incorporated by reference.

FIELD OF THE INVENTION

This invention relates to a new method for synthesis of polypeptides, involving the use of imines and carbon monoxide as monomers that undergo copolymerization under the catalysis of metal catalysts. This method avoids the tedious procedure involved in traditional polypeptide syntheses that uses amino acids as starting materials, but instead uses imines and carbon monoxide as monomers which undergo alternating copolymerization catalyzed by transition metals and directly form polypeptides. This copolymerization reaction is a novel type of polymerization, which is also a novel, concise method for polypeptide synthesis. The invention relates, further, to a class of new polypeptides that contain substituents at both the nitrogen and the carbon atoms, which are not accessible by other existing synthetic methods. These new polypeptides are not soluble in water and show unique and unexpected degradation properties, which will find important applications in the biomedical materials field.

BACKGROUND OF THE INVENTION

Polypeptides are an important class of biopolymers, not only serving as living biological system's structural and functional carrier, but also having broad applications in the fields of materials, catalysis and pharmaceuticals. Traditionally, polypeptide synthesis has been almost exclusively based on the use of amino acids as starting materials, which requires tedious procedures for presynthesis of amino acids and subsequent activation of the highly stable carboxyl groups, using stoichiometric amounts of special reagents, in order to form peptide bonds. Inside biological systems, this kind of synthesis is carried out by the ribosome and catalysis of relevant enzymes. Using this method, polypeptides with specific amino acid sequences can be synthesized by genetic engineering, but the method is basically limited to using natural amino acids as starting materials. Using a chemical method, synthesis of polypeptides would not be limited by the starting materials. Such methods include, for example, Liquid-Phase Coupling methods and Solid-Phase Synthesis techniques, and both are frequently used for preparation of oligopeptides, but they involve tedious steps and relatively high cost and are not suitable for the synthesis of polypeptides with high molecular weights.

For synthesizing high molecular weight polypeptides, however, the most efficient method should be the Ring-Opening Polymerisation of amino acid-N-carboxyanhydrides (NCA). This method also starts from amino acids and hence involves relatively high cost, which hindered large-scale production and application of the polypeptide materials. In addition, the Ring-Opening Polymerization method is usually used to synthesize polypeptides composed of N-unsubstituted amino acids and is rarely employed to synthesize polypeptides of the N-substituted amino acids because of steric hindrance (Ballard et al., J. Chem. Soc., 355 (1958)). To date, the only polypeptides of the later kind that have been obtained are those made from proline and sarcosine, as well as the short polypeptides from N-methylalanine (Cosani et al., Macromol., 11, 1041 (1978)).

Polypeptides composed of the natural occurring N-unsubstituted amino acids are normally water-soluble, unsuitable for direct use as such biomedical materials as those used for artificial organs. By contrast, N-substituted polypeptides, in which the water-soluble —NH functional groups have been removed, can be insoluble in water. However, such polypeptides have long been difficult to prepare due to lack of effective synthesis methods. One of the most attractive possible ways to solve the problem is to find a method to directly construct polypeptides through copolymerization of imines and carbon monoxide. Unfortunately, such a reaction has not been achieved due to the lack of suitable catalysts.

In 1998, Sen and Arndtsen reported independently the insertion of imines into an acyl-Pa bond, which represents one of the key steps for imine and carbon monoxide copolymerization. Although they were not able to obtain the expectated polypeptides, they successfully obtained amides (Kacker et al., Angew. Chem. Int. Ed., 37, 1251 (1998); Dghaym et al. Organometallics, 17, 4 (1998)). This is the first example that an imine was successfully inserted into a transition metal—carbon bond. Arndtsen et al. have also tried the possibility of using nickel and manganese carbonyl complexes to catalyze the imine insertion, but up to now the best result obtained is the formation of an amino acid unit from the single insertion of an imine and a carbon monoxide molecule into a metal—carbon bond. In the efforts towards polypeptice synthesis, even a simple dipeptide has never been obtained successfully by this method. (Davis et al., Organometallics, 19, 4657 (2000); Lafrance et al., Organometallics, 20, 1128 (2001)).

It is noted that cobalt is an important catalyst for carbonylation reactions, and has been used to catalyze copolymerization of aziridines and carbon monoxide. (Jia et al., J. Am. Chem. Soc., 24, 7282 (2002)). However, when Sen et al. tried to use such catalysts to catalyze the copolymerization of imines and carbon monoxide, they failed to obtain the expected polypeptide products, but instead obtained N-alkyl phthalimidine (Funk, et al. Helv. Chim. Acta, 89, 1687 (2006)).

Thus, the primary focus of the present invention is the finding of an effective catalyst that can be utilized to realize the copolymerization of imines and carbon monoxide to synthesize polypeptides with unique, unexpected properties, which were not obtainable previously.

SUMMARY OF THE INVENTION

This invention provides a new synthetic method for polypeptide synthesis, in particular a method using transition metal catalyst systems that can effectively catalyze the alternating copolymerization of imines and carbon monoxide to produce polypeptides.

The copolymerization provides a new method for synthesizing polypeptides via metal-catalyzed copolymerization of imines and carbon monoxide, which has been difficult to realize previously due to lack of appropriate catalysts.

The present invention thus provides polypeptides of formula (I):

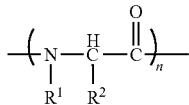

(I)

wherein R[1] and R[2] are substituents independently selected from substituted or un-substituted alkyls, and substituted or un-substituted aryl groups, and n is an integer greater than or equal to 2.

Methods for polymerizing the new polypeptides are also disclosed.

The new methods overcome the limitations of the traditional polypeptide synthesis methods (such as the ring-opening polymerization method), that use amino acids as starting materials and hence provides a shortcut pathway to polypeptides.

More importantly, the new method can easily provide polypeptides bearing substituents at both the nitrogen and the carbon atoms, which are not accessible by the previous methods. The newly obtained polypeptides, of which the hydrogen atoms at nitrogen have been substituted by other substituents, become insoluble in water due to the loss of its ability to form hydrogen bond. It is unexpectedly found that such polypeptides are quickly degradable upon dissolved in trifluoroacetic acid. These polypeptides with unique properties will find important application in fields such as biomedical materials.

DETAILED DESCRIPTION OF THE INVENTION

The polypeptides provided by the present invention have the structure as represented by formula (I):

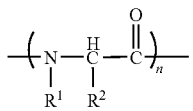

(I)

wherein R[1] and R[2] are substituents that may be independently selected from substituted or un-substituted alkyls and substituted or un-substituted aryl groups, and n is an integer that may be greater than or equal to 2.

The polypeptides according to formula (I) may include the following compounds:
(1) the polypeptides according to formula (I), wherein R[1] is substituted or un-substituted alkyl; and R[2] is substituted or un-substituted alkyl, or substituted or un-substituted aryl; provided that R[1] and R[2] are not both methyl.
(2) the polypeptides according to formula (I), wherein R[1] is substituted or un-substituted alkyl; and R[2] is substituted or un-substituted alkyl, or substituted or un-substituted aryl.
(3) the polypeptides according to formula (I), wherein R[1] is methyl; and R[2] is substituted or un-substituted alkyl, or substituted or un-substituted aryl.
(4) the polypeptides according to formula (I), wherein R[1] is methyl; and R[2] is substituted or un-substituted phenyl.
(5) the polypeptides according to formula (I), wherein R[1] is methyl; and R[2] is tert-butyl or tert-pentyl.

The imines used above have the structure as represented by formula (II):

$R^1N=CHR^2$ (II)

wherein R[1] and R[2] are substituents that have the same meaning as defined above.

Thus, the copolymerization reaction of imines and carbon monoxide may be represented by the following equation:

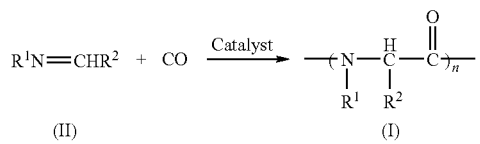

(II) (I)

wherein the catalysts used for catalyzing the copolymerization reaction are cobalt(I) complexes containing an acyl ligand, i.e., acylcobalt complexes, which have the structure as represented by formula (III):

(III)

wherein R[3] is a substituent that may be selected from substituted or un-substituted alkyls, substituted or un-substituted aryls, substituted or un-substituted alkoxyl, substituted or un-substituted aryloxyl and amino groups, and L is a ligand that may be selected from carbonyl ligands, phosphorus ligands, nitrogen ligands and isonitrile ligands.

The acylcobalt complexes according to formula (III) include the following compounds:
(1) the acylcobalt complexes according to formulation (III), wherein R[3] is substituted or un-substituted alkyl, substituted or un-substituted aryl, substituted or un-substituted alkoxy, substituted or un-substituted aryloxy, or amino; and L is carbonyl ligand, phosphorus ligand, nitrogen ligand, or isonitrile ligand.
(2) the acylcobalt complexes according to formulation (III), wherein R[3] is substituted or un-substituted alkyl, substituted or un-substituted aryl, substituted or un-substituted alkoxy, or substituted or un-substituted aryloxy, or amino; and L is carbonyl ligand.
(3) the acylcobalt complexes according to formulation (III), wherein R[3] is substituted or un-substituted alkyl; and L is carbonyl ligand.

Since in solutions the acylcobalt complexes of formula (III) actually exist in equilibrium with the corresponding alkylcobalt complexes represented by formula (IV):

$R^3-Co(CO)_3L$ (IV)

wherein R[3] is a substituent that has the same meaning as defined above, and the position of the equilibrium may be shifted between the two components, as shown by the following equation:

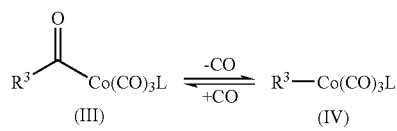

the catalyst in the polymerisation reaction actually includes precursors (IV) which can be transformed into compound (III). The precursor alkylcobalt complexes (IV) can be easily transformed into the acylcobalt complexes (III) in the presence of carbon monoxide or under the conditions of the copolymerization reaction with high pressure of carbon monoxide.

Accordingly, the alkyl complexes may also be used as precursors of the acylcobalt catalysts to catalyze the copolymerization of imines and carbon monoxide, and the alkylcobalt complexes independently prepared may be used to catalyze the copolymerization reaction.

The acylcobalt complexes precursor (IV) includes compounds represented by formula (IV):

$$R^3-Co(CO)_3L \quad (IV)$$

Compounds represented by formula (IV) include the following compounds:
(1) the acylcobalt complexes according to formulation (IV), wherein $R^3$ is substituted or un-substituted alkyl, substituted or un-substituted aryl, substituted or un-substituted alkoxy, substituted or un-substituted aryloxy, or amino; and L is carbonyl ligand, phosphorus ligand, nitrogen ligand, or isonitrile ligand.
(2) the acylcobalt complexes according to formulation (III), wherein $R^3$ is substituted or un-substituted alkyl, substituted or un-substituted aryl, substituted or un-substituted alkoxy, or substituted or un-substituted aryloxy, or amino; and L is carbonyl ligand.
(3) the acylcobalt complexes according to formulation (III), wherein $R^3$ is substituted or un-substituted alkyl; and L is carbonyl ligand.

The copolymerization reaction may be carried out in the presence of an inert organic solvent, either polar or non-polar, preferably selected from ethers, aromatic hydrocarbons, and aliphatic hydrocarbon solvents.

The reaction can be carried out under a broad range of carbon monoxide pressures, which are not critical to the reaction, but are preferably at, or higher than, 0.1013 MPa (i.e., 1 atm.), and more preferably in the range from 4.14 MPa (approximately 41 atm.) to 5.52 MPa (approx. 55 atm).

The reaction may also be performed at a broad range of temperatures. Because of the instability of the catalysts, the reaction temperature cannot be higher than 200° C., and is preferably in the range from 20° C. to 100° C., and more preferably from about 40° C. to 60° C.

In some embodiments, the catalysts used may have the structure represented by the following formula:

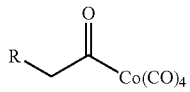

wherein R is selected from alkyl, phenyl, or substituted phenyl groups. The imines used may have the following structure:

wherein R' is selected from phenyl, substituted phenyl or alkyl groups. The polypeptides obtained may have the following structure:

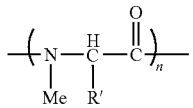

wherein R' is phenyl, substituted phenyl or alkyl; and n is an integer greater than or equal to two.

The method for polypeptide synthesis may be accomplished by the following procedures:
(1) Into an autoclave filled with CO gas is added a dry inert solvent, followed by addition of the acylcobalt catalyst to reach a concentration of 0.1 mM-1 M, preferably 1-100 mM. The CO pressure is increased to reach more than 0.1013 MPa, most preferably in the range of 4.14-5.52 MPa. The acylcobalt catalyst is allowed to age for it to transform from the types with partial loss of carbonyl to the acylcobalt form described above, with the ageing time ranging from 0.5-24 hours, preferably 6-12 hrs.
(2) After release of pressure, imines are added and the valve is closed. Carbon monoxide is pressurized again to more than 0.1013 MPa, preferably 4.14-5.52 MPa, with agitation, and the reaction is heated with an oil bath to 20-100° C., preferably 40-60° C.
(3) After completion of the reaction, the reaction mixture is cooled down, pressure is released, the vessel is opened, and the solvent is removed from the liquid product under vacuum, to give the polypeptide products.

The solvents used in the present invention are selected from alkanes (which include, but are not limited to, n-pentane, n-hexane, cyclohexane, n-heptane, n-octane, n-nonane, n-decane, petroleum ethers, and the like); aromatic hydrocarbons (which include, but are not limited to, benzene, toluene, o-dimethylbenzene, m-dimethylbenzene, p-dimethylbenzene, ethylbenzene, chlorobenzene, and the like); and ethers (which include, but are not limited to, ethyl ether, n-propyl ether, isopropyl ether, n-butyl ether, dimethoxyethane, diethoxyethane, dimethoxypropane, dioxane, methoxybenzene, and the like), esters (which include, but are not limited to, methyl acetate, ethyl acetate, and the like), amides (which include, but are not limited to, N,N-dimethylformate, N,N-dimethyl acetamides, N-methylpyrrolidinone, and the like) and nitriles (which include, but are not limited to, acetonitrile, phenylnitrile, and the like). Solvents are preferably selected from alkanes, such as n-hexane, and ethers, such as dioxane.

The term "substituted or un-substituted alkyls" used in the present invention means alkyls that are unsubstituted or have substituents at one or more positions, which include, but are not limited to, methyl, ethyl, methoxymethyl, methoxyethyl, phenoxymethyl, phenoxyethyl, benzyloxymethyl, benzyloxyethyl, phthalimidomethyl methyl, fluoromethyl, fluoroethyl, n-propyl, iso-propyl, n-butyl, iso-butyl, sec-butyl, n-amyl, n-hexyl, n-heptyl, n-octyl, n-nonyl, n-decyl, cyclopropyl, cyclobutyl, cyclopentyl, ethoxyl cyclopentyl, cyclohexyl, tert-butyoxyl cyclo-hexyl, benzyloxycyclohexyl, cycloheptyl, cycloctyl, cyclononyl, cyclodecyl, benzyl, 2-phenylethyl, 3-phenylpropyl, naphthylmethyl, 4-methoxybenzyl, and the like. Alkyl groups are preferably selected from methyl, ethyl, tert-butyl, tert-amyl and benzyl groups.

The term "substituted or un-substituted aryls" used in the invention means that any aryls that are unsubstituted of have substitutents at one or more positions, which include, but are not limited to, phenyl, tolyl, methoxylphenyl, ethylphenyl, ethoxyphenyl, propylphenyl, trimethylphenyl, naphthyl, pyridyl, furfuryl, pyrrolyl, thienyl, and the like. Aryl groups are preferably selected from phenyl, tolyl and methoxyphenyl groups.

The term "substituted or un-substituted alkoxy" means alkoxy groups that are unsubstituted or have substituents at one or more positions, which include, but are not limited to, methoxy, ethoxy, n-propyloxy, iso-propyloxy, tert-butoxy, phenoxy, cyclopentyloxy, cyclohexyloxy, 2-phenylethoxy, 3-phenylpropyloxy, 2-phenyloxyethoxy, 3-phenoxypropyloxy, fluoroethoxy, heptyloxy, octyloxy, nonyloxy, decyloxy, cyclopropyloxy, cyclobutyloxy, cyclopentyloxy, cyclohexyloxy, cycloheptyloxy, cyclooctyloxy, and the like. Alkoxy groups are preferably selected from methoxy, ethoxy and phenoxy groups.

The term "substituted or un-substituted aryloxy" means aryloxy groups that are unsubstituted or have substituents at one or more positions, which include, but are not limited to, phenoxy, methylphenoxy, ethylphenoxy, propylphenoxy, naphthyloxy, pyridyloxy, pyrrolyloxy, pyranoxy, furfuryloxy, thiophenyloxy, and the like. Aryloxy groups are preferably selected from phenoxy and methylphenoxy groups.

The term "amino group" includes but is not limited to dimethylamino, diethylamino, dipropylamino, di-iso-propylamino, dibenzylamino, cycloamylamino, cyclcohexamino, and the like. Amino groups are preferably selected from cycloamylamino and cyclcohexamino groups.

The term "phosphorus ligands" means phosphine and phosphite ligands that includes, but is not limited to, trimethylphosphine, triethylphosphine, tripropylphosphine, tributylphosphine, tri(cyclohexyl)phosphine, triphenylphosphine, tri(o-methylphenyl)phosphine, tri(m-methylphenyl)phosphine, tri(p-methylphenyl)phosphine, trimethylphosphite, triethylphosphite, tripropylphosphite, tributylphosphite, triphenylphosphite, tritolylphosphite, and the like. Phosphorus ligands are preferably selected from triphenylphosphine, tri(o-methylphenyl)phosphine and triphenylphosphite.

The term "nitrogen ligands" includes but is not limited to trimethylamine, triethylamine, tripropylamine, tributylamine, N,N-dimethyl aniline, pyridine, quinolines, and the like. The preferred nitrogen ligand is pyridine.

The term "isonitrile ligands" includes, but is not limited to, methylnitrile, ethylnitrile, n-propylnitrile, iso-propylnitrile, n-butylnitrile, tert-butylnitrile, benzylnitrile, phenylnitrile, and the like. The preferred isonitrile ligand is tert-butylnitrile.

As it is well-known, metal-catalyzed alternating copolymerization of imines and carbon monoxide is a reaction that has long been highly desirable but difficult to realize. The acylcobalt(I) catalysts provided by this invention can effectively catalyze this reaction to give polypeptides and therefore realize the copolymerization reaction for the first time.

Therefore, this invention has opened up a new efficient route for synthesis of polypeptides. The newly discovered route can avoid the tedious procedures for synthesis and activation of amino acids involved in the traditional synthetic methods, which makes polypeptide synthesis greatly simplified.

Meanwhile, as imines can be easily prepared from readily available aldehydes and amines, and as carbon monoxide is also a plentiful and cheap chemical feedstock, this synthetic method is a very convenient, economic and efficient route to synthesize polypeptides, which is especially suitable for large scale production of polypeptide materials.

Of particular note is that this method can be utilized to synthesize polypeptides that contain substituents at both the nitrogen and the carbon atoms, which are not obtainable by other existing methods. The newly obtained polypeptides are no longer soluble in water, a useful property for application as biomedical materials. In addition, the polypeptides obtained are readily degradable by some acids, such as trifluoroacetic acid. This property is unexpected and very different from the properties of N-unsubstituted polypeptides and may find important applications.

The various aspects of the invention will be appreciated more fully in light of the following illustrative examples.

EXAMPLES

Example 1

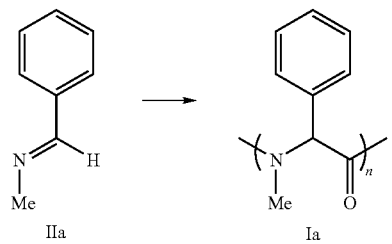

To a 300 mL autoclave of stainless steel were added 50 mL dry dioxane and 3 mL (6 mmol) of the 2.0 M solution of the acylcobalt catalyst (III: $R^3$=PhCH$_2$, L=CO) in hexane in an atmosphere of carbon monoxide. After closing the valve, the pressure of carbon monoxide was raised to 5.52 MPa, and the autoclave was allowed to stand at room temperature for 12 hours. After releasing pressure, 1.0 g (66 mol) of imine IIa was added to the autoclave. After closing the valve, the pressure of carbon monoxide was increased to 5.52 MPa once again. The mixture in the autoclave was heated in an oil-both at 50° C. while magnetically stirred for 12 hours. After cooling to room temperature, the pressure was released and the reactor was opened. The resulting solution was a brownish black liquid. The solvent was removed under vacuum to afford a brownish black glutinous material. A small amount of n-hexane was added to the brownish black glutinous material, and sufficient agitation and washing were applied to remove impurities (unreacted monomers, etc) to afford a solid powder. After filtration, the solid was collected to afford the product of polypeptide Ia as an off-white powdery solid. $^1$H NMR (400 MHz, Cl$_2$CDCDCl$_2$): δ 7.17 (bs, 5H, Ph), 6.50 (bs, 1H, CH), 2.57 (bs, 3H, Me). $^{13}$C NMR (125 MHz, Cl$_2$CDCDCl$_2$): δ 171.1 (CO), 134.3 (Ph), 129.5 (Ph), 59.5 (CH), 33.2 (Me). IR (KBr): $v_{co}$ 1647 cm$^{-1}$.

Example 2

Example 1 was repeated using 3 mmol of acylcobalt catalyst (III). Polypeptide Ia was obtained as an off-white powdery solid.

Example 3

Example 1 was repeated using hexane as the diluent. A crude product of polypeptide Ia was obtained as an off-white powdery solid.

Example 4

Example 1 was repeated, except the imine monomer was added quickly after addition of the catalyst, without pressurizing the catalyst solution with 800 psi of carbon monoxide overnight. A crude product of polypeptide Ia was obtained as an off-white powdery solid.

Example 5

Example 1 was repeated using cobalt complex (III: $R^3$=CH$_3$, L=PPh$_3$). A crude product of polypeptide Ia was obtained as an off-white powdery solid.

Example 6

Example 1 was repeated using cobalt complex (IV: $R^3$=PhOCH$_2$, L=CO). A crude product of polypeptides Ia was obtained as an off-white powdery solid.

Example 7

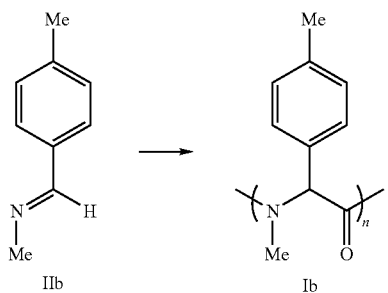

IIb → Ib

Example 1 was repeated using imine IIb. A crude product of polypeptide Ib was obtained as an off-white powdery solid. $^1$H NMR (400 MHz, Cl$_2$CDCDCl$_2$): δ 6.98 (bs, 4H, C$_6$H$_4$), 6.48 (bs, 1H, CH), 2.56 (bs, 3H, MeN), 2.16 (bs, 3H, Me). $^{13}$C NMR (125 MHz, Cl$_2$CDCDCl$_2$): δ 171.2 (CO), 138.9 (C$_6$H$_4$), 131.2 (C$_6$H$_4$), 130.1 (C$_6$H$_4$), 59.1 (CH), 33.1 (MeN), 21.7 (Me). IR (KBr): ν$_{co}$ 1647 cm$^{-1}$.

Example 8

Example 7 was repeated using 3 mmol of the acylcobalt catalyst (III) ($R^3$=PhCH$_2$, L=CO). A crude product of polypeptide Ib was obtained as an off-white powdery solid.

Example 9

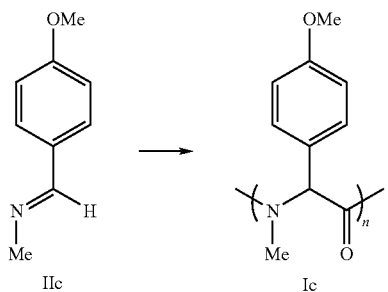

IIc → Ic

Example 1 was repeated using imine IIc. A crude product of polypeptide Ic was obtained as an off-white powdery solid. $^1$H NMR (400 MHz, Cl$_2$CDCDCl$_2$): δ 6.98 (bs, 2H, C$_6$H$_4$), 6.68 (bs, 2H, C$_6$H$_4$), 6.42 (bs, 1H, CH), 3.60 (bs, 3H, MeO), 2.54 (bs, 3H, MeN). $^{13}$C NMR (125 MHz, Cl$_2$CDCDCl$_2$): δ 171.3 (CO), 159.9 (C$_6$H$_4$), 131.0 (C$_6$H$_4$), 125.9 (C$_6$H$_4$), 114.9 (C$_6$H$_4$), 59.2 (CH), 55.9 (MeO), 33.1 (MeN). IR (KBr): ν$_{co}$ 1646 cm$^{-1}$.

Example 10

Example 9 was repeated using 3 mmol of the acylcobalt catalyst (III) ($R^3$=PhCH$_2$, L=CO). A crude product of polypeptide Ic was obtained as an off-white powdery solid.

Example 11

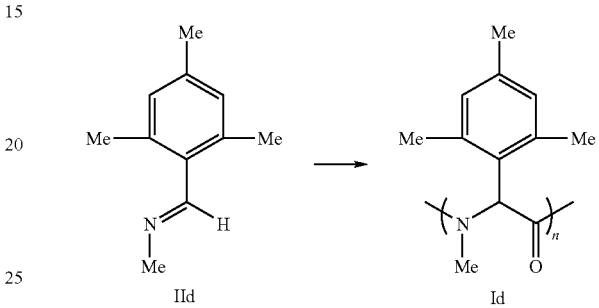

IId → Id

Example 1 was repeated using imine IId. A crude product of polypeptide Id was obtained as an off-white powdery solid. $^1$H NMR (400 MHz, Cl$_2$CDCDCl$_2$): δ 6.69 (bs, 2H, C$_6$H$_2$), 6.31 (bs, 1H, CH), 2.85-2.33 (bs, 3H, MeN), 2.05 (bs, 3H, 3Me). $^{13}$C NMR (125 MHz, Cl$_2$CDCDCl$_2$): δ172.1 (CO), 138.6 (C$_6$H$_2$), 130.9 (C$_6$H$_2$), 58.2 (CH), 31.8 (MeN), 21.4 (3Me). IR (KBr): ν$_{co}$ 1648 cm$^{-1}$.

Example 12

Example 11 was repeated using 3 mmol of acylcobalt catalyst (III) ($R^3$=PhCH$_2$, L=CO). A crude product of polypeptide Id was obtained as an off-white powdery solid.

Example 13

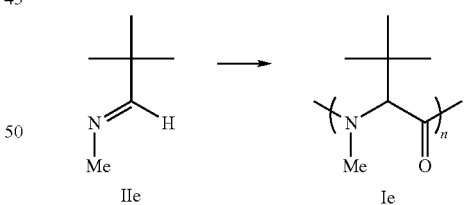

IIe → Ie

Under a carbon monoxide atmosphere, to a 300 mL autoclave of stainless steel were added 50 mL dry dioxane and 1.5 mL acylcobalt catalyst (III) ($R^3$=PhCH$_2$, L=CO) in hexane (2.0 M, 3 mmol). After closing the valve, the pressure of carbon monoxide was raised to 5.52 MPa, and autoclave was allowed to stand at room temperature for 12 hours. After pressure release, 1.0 g (66 mol) of imine IIe was added to the autoclave. After closing the valve the pressure of carbon monoxide was increased to 5.52 MPa once again. The mixture in the autoclave was heated in an oil bath at 50° C. while magnetically stirring for 12 hours. After cooling to room temperature, the pressure was released and the reactor was opened. The resulting solution was a yellow clear solution.

The solvent was removed to afford the product of polypeptide Ie as an off-white powdery solid. $^1$H NMR (400 MHz, Cl$_2$CDCDCl$_2$): δ 5.32~4.89 (m, 1H, CH), 2.94 (bs, 3H, MeN), 0.80 (bs, 9H, t-Bu). $^{13}$C NMR (125 MHz, Cl$_2$CDCDCl$_2$): δ 171.15 (CO), 57.53 (CH), 37.12 (tert-C), 34.25 (MeN), 28.33 (3Me). IR (KBr): $v_{co}$ 1641 cm$^{-1}$.

Example 14

Example 13 was repeated using 1.5 mmol of acylcobalt catalyst (III) (R$^3$=PhCH$_2$, L=CO). A crude product of polypeptide Ie was obtained as an off-white powdery solid.

Example 15

Example 13 was repeated using 1.0 mmol of acylcobalt catalyst (III) (R$^3$=PhCH$_2$, L=CO). A crude product of polypeptides Ie was obtained as an off-white powdery solid.

Example 16

Example 13 was repeated using 0.66 mmol of acylcobalt catalyst (III) (R$^3$=PhCH$_2$, L=CO). A crude product of polypeptide Ie was obtained as an off-white powdery solid.

Example 17

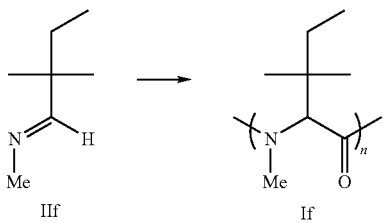

Example 13 was repeated using imine IIf. A crude product of polypeptide If was obtained as an off-white powdery solid. $^1$H NMR (400 MHz, Cl$_2$CDCDCl$_2$): δ 5.39~4.96 (m, 1H, CH), 2.95 (bs, 3H, MeN), 1.05 (m, 2H, CH$_2$), 0.82 (m, 6H, 2Me), 0.64 (bs, 3H, Me). $^{13}$C NMR (125 MHz, Cl$_2$CDCDCl$_2$): δ 171.22 (CO), 56.38 (CH), 39.97 (tert-C), 34.66 (MeN), 32.75 (CH$_2$), 24.42 (2Me), 8.86 (Me). IR (KBr): $v_{co}$ 1640 cm$^{-1}$.

Example 18

Example 17 was repeated using 1.5 mmol of the cobalt catalyst. A crude product of polypeptide If was obtained as a powdery solid.

Example 19

Example 17 was repeated using 0.82 mmol of acylcobalt catalyst (III) (R$^3$=PhCH$_2$, L=CO). A crude product of polypeptide If was obtained as an off-white powdery solid.

Example 20

Example 17 was repeated using 0.66 mmol of acylcobalt catalyst (III) (R$^3$=PhCH$_2$, L=CO). A crude product of polypeptide If was obtained as an off-white powdery solid.

The experimental results obtained in Examples 1-20 are presented in Table 1. Unless otherwise stated in a table footnote, the reactions were carried out at 50° C. and 5.52 MPa of carbon monoxide pressure, using dioxane as the solvent

TABLE 1

Results of Copolymerization of Imines and CO to Produce Polypeptides

| Entry | Imines | Molar Ratio (imine/catalyst) | Time (h) | Poly-peptides | Yields (%) | $M_n$ ($10^3$) | $M_w/M_n$ |
|---|---|---|---|---|---|---|---|
| 1 | IIa | 11:1 | 6 | Ia | 73 | 2.4 | 1.16 |
| 2 | IIa | 22:1 | 12 | Ia | 38 | 2.4 | 1.16 |
| 3 | IIa[1] | 11:1 | 6 | Ia | 40 | 1.8 | — |
| 4 | IIa[2] | 11:1 | 6 | Ia | 73 | 2.5 | 1.18 |
| 5 | IIa[3] | 11:1 | 6 | Ia | 30 | 1.8 | — |
| 6 | IIa[4] | 11:1 | 6 | Ia | 67 | 2.0 | — |
| 7 | IIb | 11:1 | 6 | Ib | 100 | 3.2 | 1.23 |
| 8 | IIb | 22:1 | 12 | Ib | 54 | 3.6 | 1.39 |
| 9 | IIc | 11:1 | 12 | Ic | 100 | 4.1 | 1.28 |
| 10 | IIc | 22:1 | 12 | Ic | 59 | 4.1 | 1.22 |
| 11 | IId | 11:1 | 12 | Id | 75 | 1.9 | — |
| 12 | IId | 22:1 | 12 | Id | 31 | 1.8 | — |
| 13 | IIe | 22:1 | 12 | Ie | 100 | 8.2 | 1.29 |
| 14 | IIe | 44:1 | 12 | Ie | 100 | 11.8 | 1.22 |
| 15 | IIe | 66:1 | 12 | Ie | 100 | 18.5 | 1.18 |
| 16 | IIe | 100:1 | 24 | Ie | 100 | 28.8 | 1.18 |
| 17 | IIf | 22:1 | 12 | If | 100 | 4.3 | 1.18 |
| 18 | IIf | 44:1 | 24 | If | 100 | 8.0 | 1.15 |
| 19 | IIf | 80:1 | 36 | If | 100 | 13.7 | 1.14 |
| 20 | IIf | 100:1 | 48 | If | 100 | 19.4 | 1.17 |

[1]Using hexane as the reaction solvent.
[2]The catalyst is not pre-pressurized with CO before addition of imines, the catalyst system is a mixture of acylcobalt and alkylcobalt.
[3]Using the cobalt complex (III: R$^3$ = CH$_3$ and L = PPh$_3$) as the catalyst.
[4]Using the cobalt complex (IV: R$^3$ = PhOCH$_2$ and L = CO) as the catalyst.

Example 21

Polypeptide If obtained above, with molecular weight M$_n$=19,000 dalton, was dissolved in trifluoroacetic acid. After standing at room temperature for 24 hours, GPC analysis indicates that the molecular weight was reduced to M$_n$=800 dalton.

While the present invention has been described and exemplified above, it is to be understood that the invention is not limited to the details of the illustrative embodiments and examples, and that it may be embodied with various changes and modifications which may occur to those skilled in the art, without departing from the invention defined in the following claims.

What is claimed is:

1. Polypeptide homopolymers of formula (I) made by copolymerization of imines and carbon monoxide:

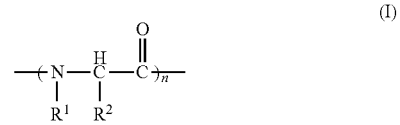

wherein R$^1$ and R$^2$ are substituents independently selected from the group consisting of substituted or un-substituted alkyl groups, and substituted or un-substituted aryl groups and wherein n is equal or greater than 2.

2. The polypeptide homopolymers of claim 1, wherein R$^1$ is a methyl group, and R$^2$ is selected from the group consisting of substituted or un-substituted alkyl groups.

3. The polypeptide homopolymers of claim 1, wherein R$^1$ is a methyl group, and R$^2$ is selected from the group consisting of substituted or un-substituted aryl groups.

4. The polypeptide homopolymers of claim 1, wherein $R^1$ is a methyl group, and $R^2$ is a phenyl, 4-methylphenyl, 4-methoxylphenyl or 2,4,6-trimethylphenyl group.

5. A method for synthesis of polypeptides, comprising the steps of:
(1) adding to an autoclave reactor an anhydrous solvent followed by an acylcobalt catalyst;
(2) adding to the autoclave reactor carbon monoxide with a pressure higher than 0.1013 MPa followed by an imine monomer;
(3) heating said reactor and stirring the contents until said amine and said carbon monoxide polymerize to form a polypeptide; and
(4) removing the solvent from the reactor upon completion of the reaction to obtain said polypeptide as a solid product; wherein the acylcobalt catalyst has a structure of the following formula:

$$R\text{-}C(=O)\text{-}Co(CO)_4$$

wherein R is selected from the group consisting of alkyl, phenyl, and substituted phenyl groups; wherein the imine monomer has the following structure:

MeN=CHR' and the polypeptide product has the following structure:

$$-(N(Me)\text{-}CH(R')\text{-}C(=O))_n-$$

wherein R' is selected from the group consisting of phenyl, substituted phenyl and alkyl groups, and n is an integer greater than or equal to 2.

6. A method for synthesizing a polypeptide having the structure of formula (I):

$$-(N(R^1)\text{-}CH(R^2)\text{-}C(=O))_n-\quad\text{(I)}$$

the method comprising copolymerizing in the presence of a transition metal catalyst an imine monomer having the structure of formula (II):

$$R^1N=CHR^2\quad\text{(II)}$$

and carbon monoxide, wherein $R^1$ and $R^2$ are substituents independently selected from the group consisting of substituted and un-substituted alkyl groups, and substituted and un-substituted aryl groups, and n is an integer greater than or equal to 2.

7. The method of claim 6, wherein said transition metal catalyst comprises a cobalt(I) complex with an acyl ligand according to formula(III):

$$R^3\text{-}C(=O)\text{-}Co(CO)_3L\quad\text{(III)}$$

8. The method of claim 7, wherein $R^3$ is selected from the group consisting of substituted and un-substituted alkyls, substituted and unsubstituted aryls, substituted and un-substituted alkoxy, substituted and un-substituted aryloxy and amino groups; and L is a carbonyl ligand.

9. The method of claim 7, wherein $R^3$ is selected from the group consisting of substituted and un-substituted alkyls, and L is a carbonyl ligand.

10. The method of claim 7, wherein $R^3$ is methyl or benzyl and L is a carbonyl ligand.

11. The method of claim 6, wherein said transition metal catalyst is a precursor compound which can be transformed into said acylcobalt catalyst of formula (III) under the conditions of said copolymerization reaction.

12. The method of claim 11, wherein said precursor compound is a cobalt compound according to formula (IV):

$$R^3Co(CO)_3L\quad\text{(IV)}$$

where $R^3$ is selected from the group consisting of substituted and un-substituted alkyls, substituted and un-substituted aryls, substituted and un-substituted alkoxy, substituted and un-substituted aryloxy and amino groups; and L is a ligand selected from the group consisting of carbonyl, phosphorus, nitrogen and isonitrile ligands.

13. The method of claim 11, wherein $R^3$ is selected from the group consisting of substituted and un-substituted alkyls, substituted and un-substituted aryls, substituted and un-substituted alkoxy, substituted and un-substituted aryloxy and amino groups; and L is a carbonyl ligand.

14. The method of claim 11, wherein $R^3$ is a substituted or unsubstituted alkyl group and L is a carbonyl ligand.

15. The method of claim 7, wherein the reaction is carried out in an inert solvent selected from ethers, alkanes and aromatic hydrocarbons.

16. The method of claim 7, wherein the reaction temperature is not higher than 200° C.

17. The method of claim 7, wherein the reaction is performed under pressure of carbon monoxide between 0.1 and 100 MPa.

18. The polypeptide homopolymers of claim 1, wherein $R^1$ is a methyl group, and $R^2$ is selected from the group consisting of substituted or un-substituted alkyl groups and substituted or unsubstituted aryl groups.

19. The polypeptide homopolymers of claim 1, wherein $R^1$ is a methyl group and $R^2$ is a tert-butyl or tert-amyl group.

* * * * *